(12) United States Patent
Silver

(10) Patent No.: US 8,267,957 B1
(45) Date of Patent: Sep. 18, 2012

(54) COMPRESSOR WITH EXTENDED RATCHET BAR FEATURE

(75) Inventor: William J. Silver, Grafton, MA (US)

(73) Assignee: Holmed Corporation, South Easton, MA (US)

( * ) Notice: Subject to any disclaimer, the term of this patent is extended or adjusted under 35 U.S.C. 154(b) by 1014 days.

(21) Appl. No.: 11/956,914

(22) Filed: Dec. 14, 2007

(51) Int. Cl.
*A61B 17/00* (2006.01)

(52) U.S. Cl. ............ 606/205; 606/208; 606/105

(58) Field of Classification Search ............ 606/86 A, 606/90, 205–208, 86 B, 914–916, 105; 81/313, 81/314, 331, 336, 338–340, 319, 324, 325, 81/315, 420

See application file for complete search history.

(56) References Cited

U.S. PATENT DOCUMENTS

| | | | | |
|---|---|---|---|---|
| 507,973 | A * | 10/1893 | Cox ................... | 81/336 |
| 887,006 | A * | 5/1908 | Moore ............... | 81/315 |
| 1,158,345 | A * | 10/1915 | Weaver ............. | 81/320 |
| 1,957,113 | A * | 5/1934 | Smith ............... | 292/238 |
| 3,470,872 | A * | 10/1969 | Grieshaber ........ | 600/217 |
| 3,661,413 | A * | 5/1972 | Silva ................ | 292/238 |
| 5,102,412 | A * | 4/1992 | Rogozinski ....... | 606/86 A |
| 5,122,130 | A * | 6/1992 | Keller .............. | 606/86 A |
| 5,334,198 | A * | 8/1994 | Hart et al. ........ | 606/52 |
| 5,370,659 | A * | 12/1994 | Sakashita ......... | 606/205 |
| 5,591,167 | A * | 1/1997 | Laurain et al. .... | 606/86 A |
| 5,697,933 | A * | 12/1997 | Gundlapalli et al. | 606/96 |
| 5,702,453 | A | 12/1997 | Rabbe et al. | |
| 5,810,878 | A | 9/1998 | Burel et al. | |
| 6,042,540 | A * | 3/2000 | Johnston et al. .. | 600/213 |
| 6,146,386 | A | 11/2000 | Blackman et al. | |
| 6,159,217 | A * | 12/2000 | Robie et al. ....... | 606/88 |
| 6,261,296 | B1 | 7/2001 | Aebi et al. | |
| 6,945,933 | B2 * | 9/2005 | Branch et al. ..... | 600/210 |
| 7,189,234 | B2 | 3/2007 | Zuckerman et al. | |
| 7,189,244 | B2 | 3/2007 | Newton et al. | |
| 7,722,649 | B2 * | 5/2010 | Biedermann et al. | 606/257 |
| 7,846,177 | B2 * | 12/2010 | Carpenter et al. .. | 606/205 |
| 2001/0031969 | A1 | 10/2001 | Aebi et al. | |
| 2002/0095153 | A1 * | 7/2002 | Jones et al. ....... | 606/61 |
| 2007/0100347 | A1 * | 5/2007 | Stad et al. ......... | 606/90 |
| 2008/0077156 | A1 * | 3/2008 | Emstad ............. | 606/105 |
| 2009/0223332 | A1 * | 9/2009 | Gao ................... | 81/420 |
| 2010/0280560 | A1 * | 11/2010 | Brumfield et al. .. | 606/86 A |

* cited by examiner

*Primary Examiner* — Eduardo C Robert
*Assistant Examiner* — Jan Christopher Merene
(74) *Attorney, Agent, or Firm* — Cesari and McKenna, LLP

(57) ABSTRACT

In one embodiment, a surgical instrument includes a first and second lever arms coupled by a first pivot. A ratchet bar is coupled to the first lever arm by a second pivot. The ratchet bar has a toothed portion extending from an interior face of the first lever arm and a paddle portion extending from an exterior face of the first lever arm. A catch is disposed at a proximate end of the second lever arm and arranged to engage teeth of the toothed portion of the ratchet bar. Engagement with the teeth couples the proximate ends of the first and second lever arms. The ratchet bar is further arranged to rotate about the second pivot in response to downward pressure upon the paddle. Depression of the paddle causes the teeth of disengage the catch, decoupling the first and second lever arms.

16 Claims, 4 Drawing Sheets

COMPRESSOR WITH EXTENDED RATCHET BAR FEATURE

BACKGROUND

1. Technical Field

The present invention relates generally to surgical instruments and more specifically to surgical compressors and similar instruments.

2. Background Information

In some surgical procedures, a surgeon may need to exert compressive force on objects disposed within the human body. One such surgical procedure is minimally invasive spinal fusion surgery.

Minimally invasive spinal fusion surgery involves accessing the spine via a small incision and rigidly attaching two or more vertebrae with a fixation rod or other element. Typically, the surgeon first inserts an access port into the incision, to both hold open the incision and create a stable work platform. The access port typically has an expandable distal end that holds back tissue, and that rests upon bone to prevent muscle creep and stabilize the port. With an access port in place, the surgeon usually screws or otherwise is affixes bone screws or other constructs to two or more vertebrae. A spinal fixation rod is attached between the bone screws, held in place, for example, by set screws or other fasteners. The spinal fixation rod holds the vertebra in a desired spatial relationship until spinal fusion or other healing occurs.

In many cases, it is desirable for the spinal fixation rod to hold the vertebra in a compressed state. Thus, the surgeon applies compressive force between bone screws and then secures the spinal fixation rod to maintain the compressive force. To apply the compressive force, the surgeon may use a surgical compressor. Most existing surgical compressors may be classified into two general types: cable-type compressors and lever-type compressors.

Cable-type compressors typically employ a cable that wraps around bone screws. The surgeon applies tension to the cable by manipulating a ratcheting mechanism, such as a ratcheting pistol grip. The ratcheting mechanism exerts and holds tension upon the cable. The greater the tension, the greater the compression between the bone screws. While many cable-type compressors advantageously permit single-handed operation, they suffer many shortcomings. For example, it may be difficult to properly arrange the cable about the bone screws in a confined surgical space. Further, a cable-type compressor may provide unwanted mechanical advantage, rendering it difficult for the surgeon to judge the actual compression being exerted.

Lever-type compressors typically employ two lever arms arranged to resemble a pliers. The surgeon places the distal ends of the lever arms about the bone screws. By gripping and squeezing together the proximate ends of the arms, the surgeon may apply compression. To maintain the compression, such that the surgeon need not continually squeeze the lever arms together, some lever-type compressors have a spring-loaded is ratchet bar that may be used to couple the arms. The surgeon may cause the ratchet bar to lock the two lever arms in a fixed relative position to maintain compression.

One shortcoming of conventional lever-type compressors with ratchet bars is that they require two hands to operate: one hand to squeeze together the lever arms, and another hand to move the ratchet bar into place, or out of place. The need for two hands prevents the surgeon from simultaneously manipulating some other surgical instrument or performing some other task. This is especially limiting in complicated surgeries.

Accordingly there is a need for an improved surgical instrument that overcomes the shortcomings of prior designs.

SUMMARY

The shortcomings of the prior art are addressed in part by a novel surgical instrument having an extended ratchet bar feature that permits single handed operation.

In an illustrative embodiment, a compressor includes first and second lever arms coupled at a pivot point in an X-shaped arrangement. The distal ends of the lever arms have gripping extensions sized to securely fit about bone screws. The proximate ends of the lever arms may be grasped by the hand of a surgeon. A flex spring is disposed between proximate ends of the lever arms to hold them apart when the compressor is at rest. When the lever arms are squeezed together, the flex spring bends, permitting the proximate ends of the lever arms to move closer together. When this occurs, the distal ends are forced together and the gripping extensions apply compression to any objects, for example a pair of bone screws, disposed therebetween.

A first one of the lever arms is configured to have a cutout at its proximate end, the cutout extending from an interior face of the lever arm its exterior face. A ratchet bar extends through the cutout, and is held to the first lever arm by a pivot. A paddle portion of the ratchet bar extends from the exterior face of the arm, while a toothed portion of the ratchet bar, having a plurality of teeth arranged on its underside, extends from the interior face. The toothed portion is sufficiently weighted so that gravity causes the teeth to engage a catch extending from the proximate end of the second lever arm. As a surgeon squeezes the proximate ends of the lever arms together, the catch ratchets through teeth to is engage teeth progressively closer to the first lever arm. In this manner, compression applied by the surgeon's grip is maintained by the ratchet bar.

The paddle that extends from the exterior face of the ratchet bar may be depressed by the surgeon, for example by a thumb or finger. This causes the ratchet bar to pivot, so that the teeth disengage from the catch on the second lever arm, decoupling the arms. If the paddle is released, gravity causes the ratchet bar to rotate back so that the teeth reengage the catch. Accordingly, unlike prior devices, a second hand is not required to move the ratchet bar into or out of engagement with the catch, the surgeon may do so by operating the paddle with the same hand that holds the compressor.

BRIEF DESCRIPTION OF THE DRAWINGS

The description below refers to the accompanying drawings, of which.

DETAILED DESCRIPTION OF AN ILLUSTRATIVE EMBODIMENT

Figure 1:
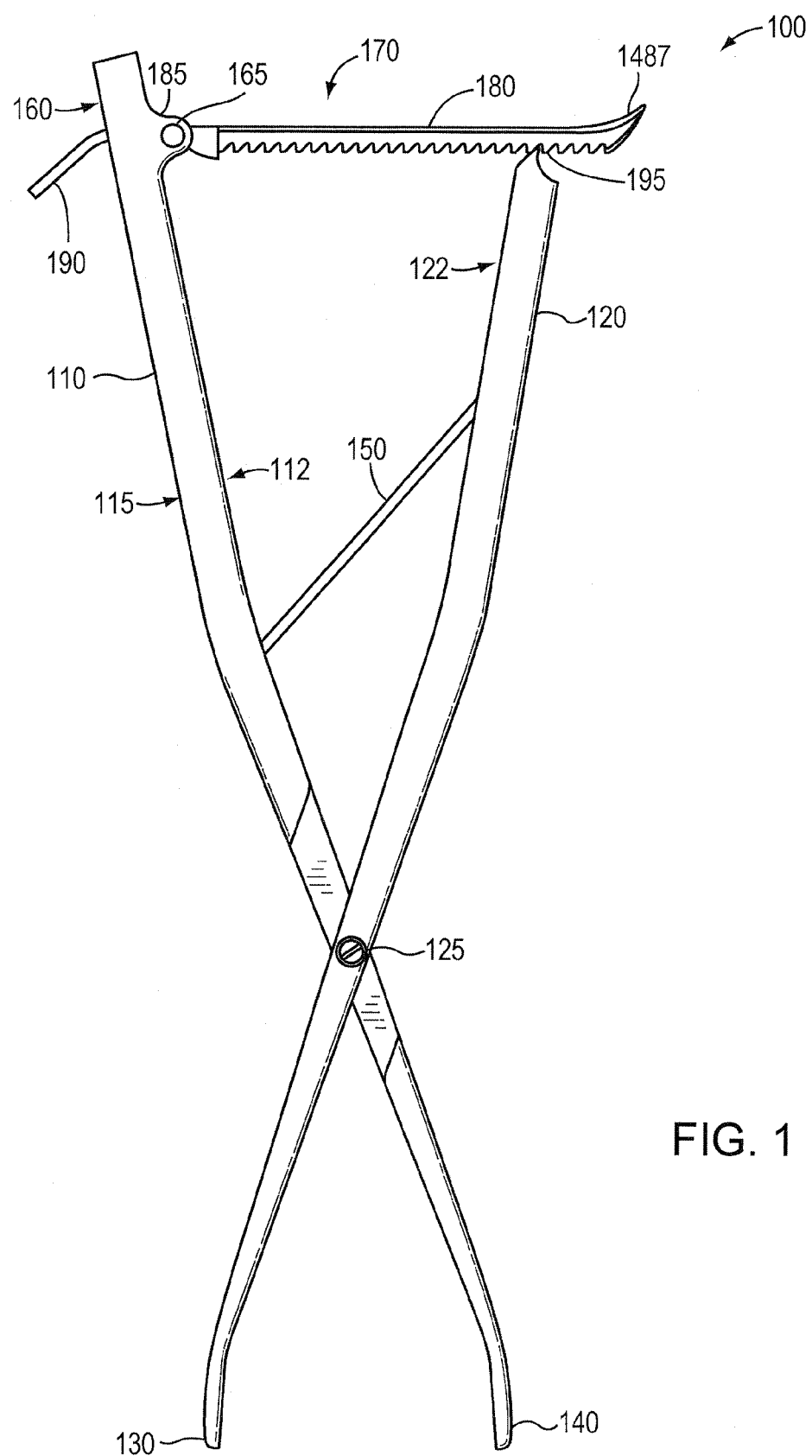
FIG. 1 is a side elevation of a compressor according to an illustrative embodiment of the present disclosure.
Figure 2:
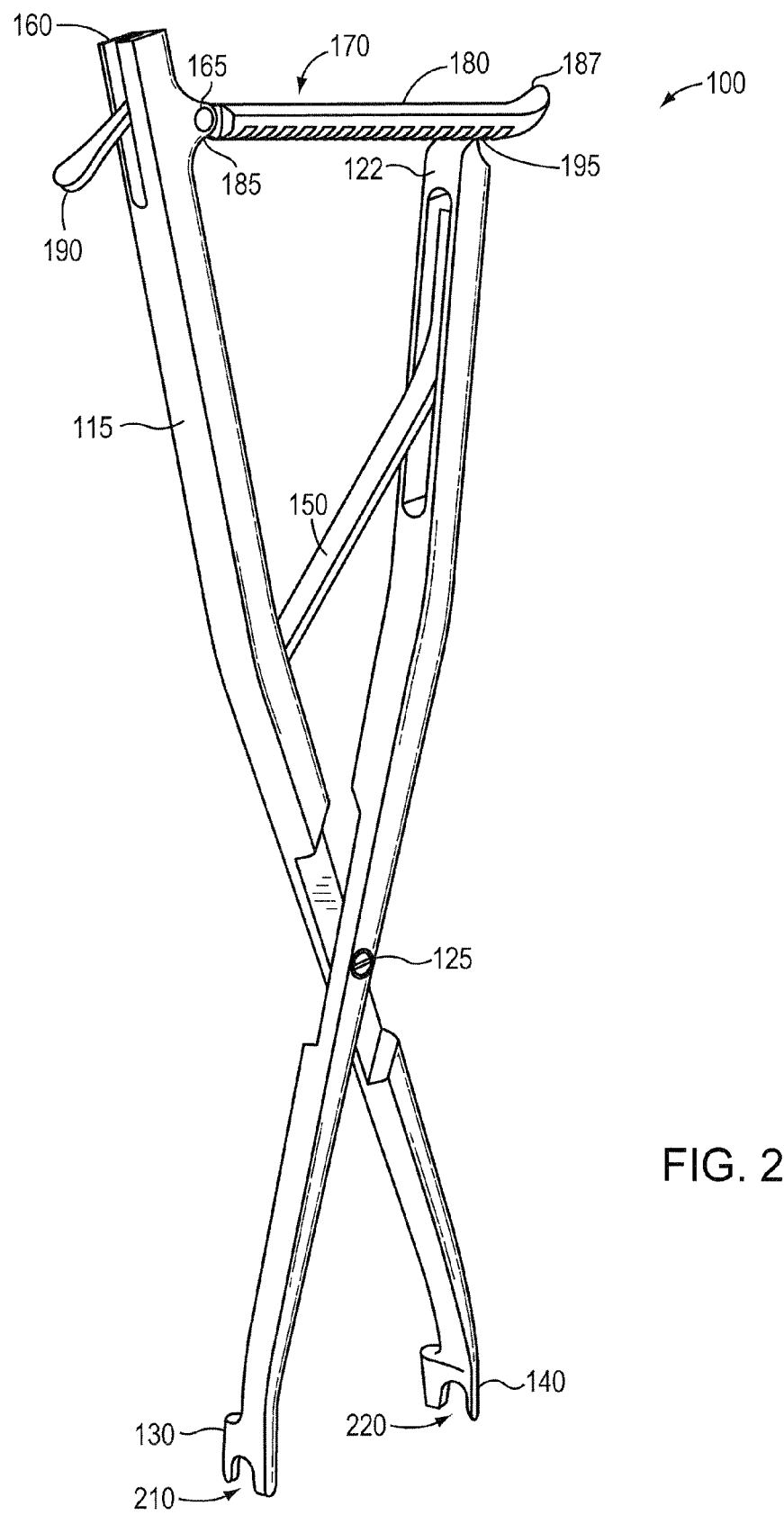
FIG. 2 is a perspective view of the compressor of FIG. 1.

As shown in the FIGS. 1 and 2, a compressor 100 according to an illustrative embodiment of the present disclosure includes first and second lever arms 110, 120 coupled in an X-shaped arrangement by a pivot 125. The distal ends of the lever arms 110, 120 have gripping extensions 130, 140 formed thereon. Depending on the particular implementation, the gripping extensions 130, 140 may be differently shaped.

Figure 3:
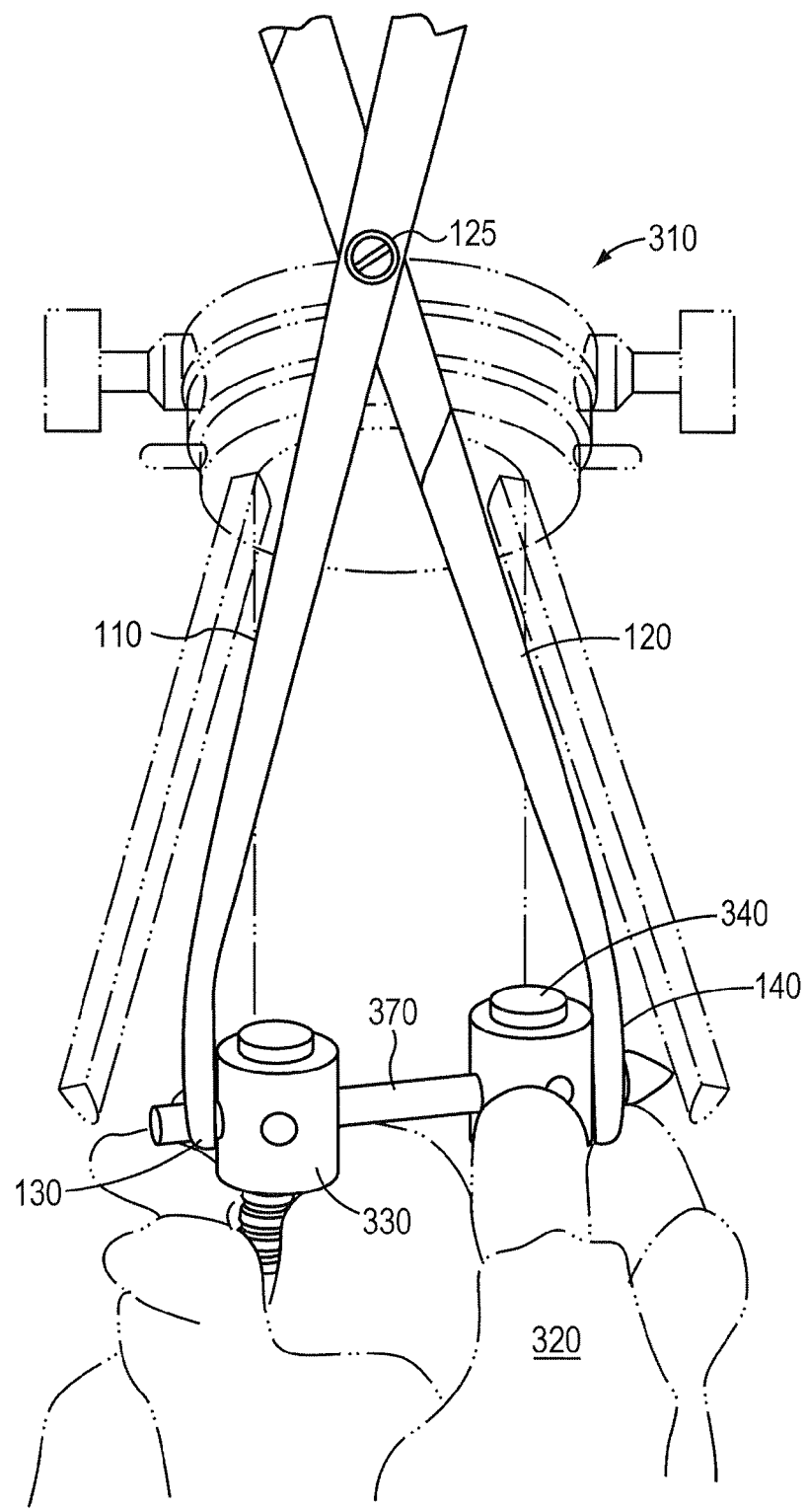
FIG. 3 is a schematic illustration of use of the compressor of FIG. 1 in a minimally invasive spinal fusion procedure.

For example, if the compressor 100 is intended for use in minimally invasive spinal fusion surgery, the gripping extensions 130, 140 may be formed to fit securely around bone screws, or other constructs, secured to a patient's spine. Referring to FIG. 3, in a typical minimally invasive spinal fusion procedure, a surgeon inserts the distal ends of the lever arms 110, 120 into a patient via an access port 310 disposed in an incision proximate the patient's spine 320. The surgeon fits the gripping extensions 130, 140 about generally cylindrical bone screws 330, 340 secured into vertebrae 350, 360. A semi-circular contour of the gripping extensions 130, 140 advantageously allows them to securely hold the generally cylindrical screws 330, 340. A spinal fixation rod 370 is typically affixed to the bone screws 330, 340, in some cases passing through them, and is typically secured by set screws. One or more openings 210, 220 (visible in FIG. 2) may be formed in the gripping extensions 130, 140 to accommodate the fixation rod 370, and allow it to extend therethrough.

Referring to FIGS. 1 and 2, the proximate ends of the lever arms 110, 120 may be thicker than the distal ends, or may be otherwise ergonomically formed, so that they may be easily held by a surgeon. A flex spring 150 is attached to the second lever arm 120 within a depression 230 by a fastener 155. The flex spring is disposed at an angle relative to the lever arms 110, 120 and holds them apart when the compressor 100 is at rest. When the lever arms 110, 120 are squeezed together, the flex spring 150 flexes toward the interior face 122 of the second lever arm to permit the proximate ends of the lever arms 110, 120 to move closer together. Resistance provided by the flex spring 150 may provide better feel to the compressor, while also causing the lever arms 110, 120 to return automatically to a convenient resting position.

The first lever arm 110 has a cutout in the form of a slot 160 at its proximate end, extending from the interior face 112 of the lever arm to its exterior face 115. Depending on the particular implementation, the cutout may be differently shaped. For example, it may alternately be fully enclosed by the structure of the first lever arm 110.

A ratchet bar 170 passes through the slot 160. The ratchet bar 170 is affixed to the first lever arm 110 by a pivot 165 located in a protrusion 185 of the lever arm 110. A toothed portion 180 of the ratchet bar 170 extends from the interior face 122 of the arm 120 while a paddle 190 extends from the exterior face 125. The toothed portion 180 includes a plurality of angular teeth, each having a first face substantially perpendicular to the length of the ratchet bar 180, and a second face at an acute angle relative to the length of ratchet bar 170. The toothed portion 180 may include a weighted tip 187, a protrusion of the ratchet bar that is intended to provide additional mass.

When the compressor 100 is held in a substantially upright orientation, gravitational force on the toothed portion 180 and weighted tip 187 causes the teeth of the ratchet bar 170 to engage a catch 195 extending from the proximate end of the second lever arm 120. As a surgeon squeezes the proximate ends of the lever arms 110, 120 together, the catch 195 ratchets through the teeth, engaging teeth progressively closer to the pivot 165. Any compression applied by the surgeon is maintained by the ratchet bar 170 which couples the arms 110, 120 and prevents their proximate ends from spreading. In contrast to some prior lever-type compressors, a hold-down spring need not be employed with the ratchet bar 170; gravitational force is generally sufficient to cause the teeth to engage the catch 195 due to the location of the teeth of the ratchet bar 170 relative to the catch 195. Force from the catch 195 is exerted parallel to the ratchet bar 170, and not upwards on the ratchet bar 170, which could cause disengagement. Elimination of a hold down spring reduces manufacturing complexity and accordingly may decrease manufacturing costs.

The paddle 190 extends from the exterior face 115 of the first lever arm 110. When the paddle 190 is subject to downward pressure by the surgeon, the ratchet bar 170 pivots upwards, such that its teeth disengage the catch 195, and the arms 110, 120 decouple. Thereafter, if the paddle is released by the surgeon, gravity causes the ratchet bar 170 to rotate back so that the teeth reengage the catch 195. Unlike some prior lever-type compressors, a second hand is not required to move the ratchet bar into, or out of, engagement with the catch 195. If the surgeon holds the compressor 100 such that the first lever arm 110 rests upon the surgeon's palm, and the second lever arm 120 rests upon the surgeon's fingers, the surgeon may readily actuate the paddle 190 with their thumb. Alternately, if the surgeon holds the compressor 100 such that the first lever arm 110 rests upon the surgeon's fingers and the second lever arm 120 rests upon the surgeon's palm, the surgeon may actuate the paddle 190 with their index finger or another finger. A variety of other one-handed modes of use may also be possible. By enabling use with one hand, the surgeon is freed to perform other surgical tasks with their other hand.

While the above description discusses an illustrative embodiment of present disclosure, it should be apparent that a number of modifications and/or additions may be made without departing from the disclosure's intended spirit and scope.

Figure 4:
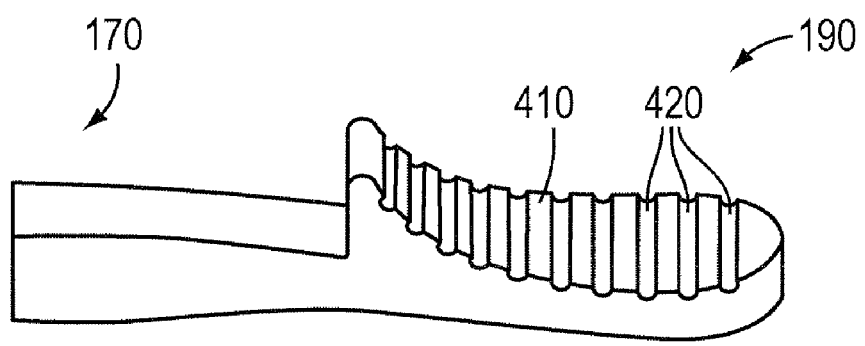
FIG. 4 is an isometric view of an example contoured paddle that may be used with the compressor of FIG. 1.

The paddle 190 may be shaped in a variety of different ways in differing implementations. In reference to FIG. 4, the paddle 190 may have a contoured upper face 410 to provide greater surface area for contacting with a surgeon's thumb or finger. Also, a plurality of transverse grooves 420, knerls, cross-hatch scores, stipples, or other features may be employed to reduce slippage that may occur should the paddle happen to become wet during a procedure.

Figure 5:
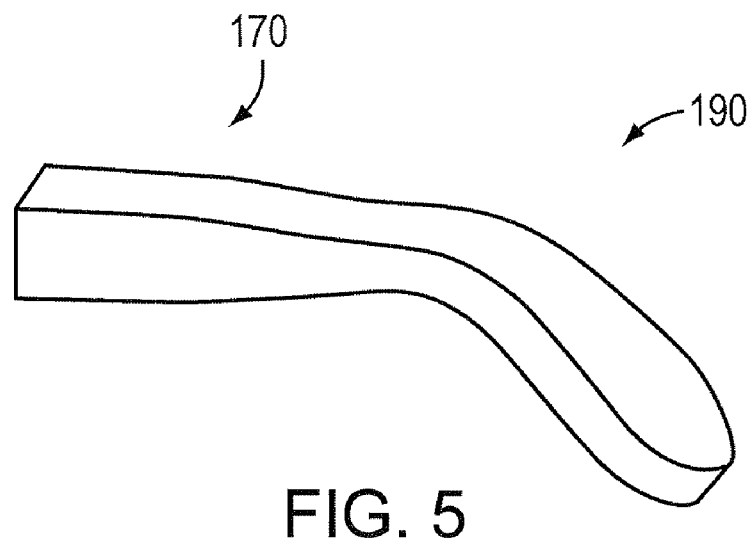
FIG. 5 is an isometric view of an example angled paddle that may be used with the compressor of FIG. 1.

In reference to FIG. 5, the paddle 190 may be angled downward with respect to the rest of the ratchet bar 170. The angle may both allow easier manipulation of the paddle by a thumb or finger, as well as advantageously limit the upward swing of the ratchet bar 170, as the angled paddle 190 will contact the exterior face 115 of the first lever arm 110 when depressed. By limiting its upward swing, the ratchet bar 170 may be maintained in an orientation sufficiently horizontal such that gravity will cause it to readily fall back upon the catch 195.

Further, the components of the compressor 100 may be constructed from a variety of different materials. While medical grade stainless steal is used in the illustrative embodiment, a variety of other materials, including other metals, plastics, composites, or combinations thereof, may alternately be employed.

Further, while the illustrative embodiment discusses a compressor, the teachings herein may be applied to other devices. For example, a surgical distractor designed to separate two objects may be constructed according to the above teachings. Such a distractor may have a cutout through which a ratchet bar having a paddle and a toothed portion is disposed. By actuating the paddle the ratchet bar may be rotated into, or out of, engagement with a catch, similar to as described above.

Further, while repeated reference is made above to minimally invasive spinal fusion surgery, the teachings herein are in no way limited to instruments used in that specific type of medical procedure, and are applicable to instruments used in a variety of different types of procedures as well as to instruments used in non-medical fields.

Accordingly, it should be understood that the above descriptions are meant to be taken only by way of example.

What is claimed is:

1. A surgical instrument comprising:
   a first lever arm having distal and proximate ends;
   a second lever arm having distal and proximate ends and coupled to the first lever arm by a first pivot;
   a ratchet bar coupled to the first lever arm by a second pivot, the ratchet bar having a toothed portion extending from an interior face of the first lever arm and a paddle extending from an exterior face of the first lever arm, the paddle disposed at a downward angle with respect to the toothed portion of the ratchet bar such that when the surgical instrument is held in a substantially upright position, with the proximate ends of the first and second lever arms arranged upward, the paddle projects downward from the toothed portion and away from the proximate end of the first lever arm; and
   a catch disposed on the second lever arm and arranged to engage teeth of the toothed portion of the ratchet bar, engagement with the teeth coupling the proximate ends of the first and second lever arms;
   wherein the ratchet bar is formed with sufficient mass such that when the surgical instrument is held in the substantially upright position, gravitational force is sufficient to cause teeth of the toothed portion of the ratchet bar to engage the catch unless downward pressure is applied upon the paddle to overcome the gravitational force, and application of downward pressure upon the paddle to overcome the gravitational force causes the teeth to disengage the catch thereby decoupling the first and second lever arms, and
   wherein the downward angle of the paddle causes the paddle to contact the exterior face of the first lever arm to limit the rotation of the ratchet bar about the second pivot and to maintain the ratchet bar in an orientation such that when the surgical instrument is held in the substantially upright position, gravity will cause the ratchet bar to fall back upon the catch absent application of downward pressure upon the paddle.

2. The surgical instrument of claim 1 wherein the first and second lever arms are sized to fit between a palm and fingers of a human hand, and wherein the paddle is located in a position where it may be depressed by one of a thumb and a finger of the human hand, to permit single-handed operation.

3. The surgical instrument of claim 1 wherein the toothed portion of the ratchet bar includes a weighted tip, the weighted tip being a protrusion of the ratchet bar that lacks teeth but that provides additional mass.

4. The surgical instrument of claim 1 wherein the paddle has a contoured upper face.

5. The surgical instrument of claim 4 wherein the contoured upper face includes a plurality of transverse grooves.

6. The surgical instrument of claim 1 wherein a flex spring is disposed between the first and second lever arms, the flex spring configured to hold the proximate ends of the first and second lever arms remote from each other when the compressor is in a resting state.

7. The surgical instrument of claim 1 wherein the ratchet bar is disposed in a cutout of the first lever arm.

8. The surgical instrument of claim 1 further comprising:
   a first gripping extension arranged at the distal end of the first lever arm and having a substantially semi-circular contour; and
   a second gripping extension arranged at the distal end of the second lever arm and having a substantially semi-circular contour.

9. The surgical instrument of claim 8 wherein the first and second gripping extensions are sized to engage cylindrical portions of bone anchors.

10. The surgical instrument of claim 1 wherein the surgical instrument is a compressor and the first and second distal ends are arranged to apply compressive force to a load.

11. The surgical instrument of claim 1 wherein the surgical instrument is a distractor and the first and second distal ends are arranged to apply separative force to a load.

12. A surgical instrument comprising:
    a first lever arm having distal and proximate ends;
    a second lever arm having distal and proximate ends and coupled to the first lever arm by a first pivot;
    a cutout at the proximate end of the first lever arm extending from an interior face of the first lever arm to an exterior face of the first lever arm;
    a ratchet bar extending through the cutout and coupled to the first lever arm by a second pivot, the ratchet bar having a toothed portion extending from the cutout at the interior face of the first lever arm and a paddle extending from the cutout at the exterior face of the first lever arm, the paddle disposed at a downward angle with respect to the toothed portion of the ratchet bar such that when the surgical instrument is held in a substantially upright position, with the proximate ends of the first and second lever arms arranged upward, the paddle projects downward from the toothed portion and away from the proximate end of the first lever arm; and
    a catch disposed at the proximate end of the second lever arm and arranged to engage teeth of the toothed portion of the ratchet bar, engagement with the teeth coupling the proximate ends of the first and second lever arms;
    wherein the ratchet bar is formed with sufficient mass such that when the surgical instrument is held in the substantially upright position, gravitational force is sufficient to cause teeth of the toothed portion of the ratchet bar to engage the catch unless downward pressure is applied upon the paddle to overcome the gravitational force, application of downward pressure upon the paddle to cause the teeth to disengage the catch thereby decoupling the first and second lever arms, and
    wherein the downward angle of the paddle causes the paddle to contact the exterior face of the first lever arm to limit the rotation of the ratchet bar about the second pivot and to maintain the ratchet bar in an orientation such that when the surgical instrument is held in the substantially upright position, gravity will cause the ratchet bar to fall back upon the catch absent application of downward pressure upon the paddle.

13. The surgical instrument of claim 12 wherein the first and second lever arms are sized to fit between a palm and fingers of a human hand, and wherein the paddle is located in a position where it may be depressed by one of a thumb and a finger of the human hand, to permit single-handed operation.

14. The surgical instrument of claim 12 wherein the toothed portion of the ratchet bar includes a weighted tip, the weighted tip being a protrusion of the ratchet bar that lacks teeth but that provides additional mass.

15. The surgical instrument of claim 12 wherein the paddle has a contoured upper face.

16. The surgical instrument of claim 15 wherein the contoured upper face includes a plurality of transverse grooves.

* * * * *

UNITED STATES PATENT AND TRADEMARK OFFICE
CERTIFICATE OF CORRECTION

| | | |
|---|---|---|
| PATENT NO. | : 8,267,957 B1 | Page 1 of 1 |
| APPLICATION NO. | : 11/956914 | |
| DATED | : September 18, 2012 | |
| INVENTOR(S) | : William J. Silver | |

It is certified that error appears in the above-identified patent and that said Letters Patent is hereby corrected as shown below:

In the Specification:

In col. 1, line 23 should read:
Surgeon usually screws or otherwise ~~is~~ affixes bone screws or In col. 1, line 57 should read:
Loaded ~~is~~ rachet bar that may be used to couple the arms. The In col. 2, line 33 should read:
Together, to catch ratchets through teeth to ~~is~~ engage teeth Signed and Sealed this
Eleventh Day of June, 2013

Teresa Stanek Rea
*Acting Director of the United States Patent and Trademark Office*